United States Patent
Harwood et al.

(10) Patent No.: US 8,268,584 B1
(45) Date of Patent: Sep. 18, 2012

(54) HYDROGEN PRODUCTION FROM MICROBIAL STRAINS

(75) Inventors: Caroline S. Harwood, Seattle, WA (US); Federico E. Rey, Brentwood, MO (US)

(73) Assignee: University of Washington, Seattle, WA (US)

( * ) Notice: Subject to any disclaimer, the term of this patent is extended or adjusted under 35 U.S.C. 154(b) by 1328 days.

(21) Appl. No.: 11/947,535

(22) Filed: Nov. 29, 2007

Related U.S. Application Data (60) Provisional application No. 60/868,223, filed on Dec. 1, 2006.

(51) Int. Cl.
*C12P 21/06* (2006.01)
*C12P 21/04* (2006.01)

(52) U.S. Cl. ...................... 435/69.1; 435/71.1

(58) Field of Classification Search .................. None
See application file for complete search history.

(56) References Cited

OTHER PUBLICATIONS

Zhang et al., "Mutagenesis and Functional Characterization of the gInB, gInA, and nifA Genes from the Photosynthetic Bacterium *Rhodospirillum rubrum* ", J. Bacteriology, 2000, 182(4):983-992.*

Rubio & Ludden, "Maturation of Nitrogenase: a Biochemical Puzzle", J. Bacteriology, 2005, 187(2):405-414.*
Dixon et al., "Mutant Forms of the Azotobacter vinelandii Transcriptional Activator NifA Resistant to Inhibition by the NifL Regulatory Protein", Journal of Bacteriology, Dec. 2002, p. 6777-6785.*
Drepper et al., "Role of GInB and GInK in Ammonium Control of Both Nitrogenase Systems in the Phototrophic Bacterium *Rhodobacter Capsulatus*,"Microbiology 149:2203-12 (2003).
Hillmer et al., "H2 Metabolism in the Photosynthetic Bacterium *Rhodopseudomonas capsulata*: Production and Utilization of H2 by Resting Cells," Journal of Bacteriology 129(2):732-39 (1977).
Joshi et al., "A Global Two Component Signal Transduction System that Integrates the Control of Photosynthesis, Carbon Dioxide Assimilation, and Nitrogen Fixation," Proc. Natl. Acad. Sci. USA 93:14515-20 (1996).

* cited by examiner

*Primary Examiner* — Suzanne M Noakes
(74) *Attorney, Agent, or Firm* — Nixon Peabody LLP (57) ABSTRACT

The present invention is directed to a method of screening microbe strains capable of generating hydrogen. This method involves inoculating one or more microbes in a sample containing cell culture medium to form an inoculated culture medium. The inoculated culture medium is then incubated under hydrogen producing conditions. Once incubating causes the inoculated culture medium to produce hydrogen, microbes in the culture medium are identified as candidate microbe strains capable of generating hydrogen. Methods of producing hydrogen using one or more of the microbial strains identified as well as the hydrogen producing strains themselves are also disclosed.

17 Claims, 6 Drawing Sheets

FIG. 1A

HYDROGEN PRODUCTION BY WILD-TYPE *R. palustris* STRAIN CGA009

| CARBON SOURCE | e⁻/O RATIO | HYDROGEN PRODUCTION ($\mu$MOLES/mg PROTEIN) | |
|---|---|---|---|
| | | NON-NITROGEN-FIXING | NITROGEN-FIXING |
| MALATE (10 mM) | 0.8 | <1 | 36 ± 6 |
| SUCCINATE (10 mM) | 1.0 | <1 | 31 ± 2 |
| ACETATE (20 mM) | 1.5 | <1 | 37 ± 5 |
| *p*-COUMARATE (4.5 mM) | 2.3 | NO GROWTH | 86 ± 26 |
| CYCLOHEXANECARBOXYLATE (5.7 mM) | 5.5 | NO GROWTH | 47 ± 8 |

| RPA OR OPERON | GENE NAME | AVG. FOLD DIFFERENCE IN EXPRESSION | | | | ANNOTATION |
|---|---|---|---|---|---|---|
| | | CGA570 | CGA571 | CGA572 | CGA574 | WILD TYPE (NF) |
| 1848-1849 | | 1.1 | 3.0 | 2.4 | 2.1 | 2.5 | UNCHARACTERIZED IRON-REGULATED MEMBRANE PROTEIN/CONSERVED HYPOTHETICAL |
| 1927-1928 | | 20 | 66 | 7.0 | 36 | 34 | UNCHARACTERIZED CONSERVED PROTEIN/FERREDOXIN-LIKE PROTEIN [2Fe-2S] |
| 2156 | | 14 | 53 | 4.9 | 19 | 32 | CONSERVED HYPOTHETICAL PROTEIN |
| 2380-2388 | | 2.6 | 8.5 | 1.0 | 3.0 | 10 | IRON (III) TRANSPORT |
| 3012-3013 | pucABd | 3.3 | 3.6 | 2.2 | 3.8 | 6.1 | LIGHT HARVESTING PROTEINS B-800-850, (LHII) |
| 4714 | | 9.2 | 40.3 | 2.7 | 22 | 19 | CONSERVED HYPOTHETICAL PROTEIN |
| 4827 | | 3.8 | 15 | 1.7 | 7.0 | 7.3 | CONSERVED HYPOTHETICAL PROTEIN |

HYDROGEN PRODUCTION FROM MICROBIAL STRAINS

This application claims the benefit of U.S. Provisional Patent Application Ser. No. 60/868,223 filed Dec. 1, 2006, which is hereby incorporated by reference in its entirety.

This invention was made with government support under grant number DE-FG02-05ER64063 awarded by the U.S. Department of Energy and by grant number W911NF-05-1-0176 awarded by the U.S. Department of Defense. The Government has certain rights in the invention.

FIELD OF THE INVENTION

The present invention generally relates to the production of hydrogen from microbial strains.

BACKGROUND OF THE INVENTION

Hydrogen biofuel has the potential to solve a variety of challenges related to the global need for a clean and sustainable form of energy. Hydrogen can be produced from a variety of domestic resources including: fossil fuels such as natural gas and coal; renewable resources such as solar, wind, and biomass; or nuclear energy. The current challenge, however, is to develop technologies for hydrogen production from these resources that are clean, efficient, and cost effective.

Photobiological processes, specifically those which involve the production of hydrogen from specialized microorganisms, offer an attractive long term renewable mechanism of hydrogen production that will minimally impact the environment (Gest, et al. "Studies on the Metabolism of Photosynthetic Bacteria. V. Photoproduction of Hydrogen and Nitrogen Fixation by *Rhodospirilum rubrum*," *J. Biol, Chem.* 182:153-170 (1950); Das, et al. "Hydrogen Production by Biological Processes: A Survey of Literature," *Int. J. Hydrogen Energy* 26:13-28 (2001); Prince & Kheshgi, "The Photobiological Production of Hydrogen: Potential Efficiency and Effectiveness as a Renewable Fuel," *Crit. Rev. Microbial.* 31:19-31 (2005)). For this technology to be commercially efficient, however, these hydrogen producers must be identified and potentially modified for optimized production.

Microbes possess two enzymes, hydrogenase and nitrogenase, which produce hydrogen either directly through fermentation, or indirectly as a by-product of other metabolic processes. Nitrogenases are chiefly involved in the conversion of nitrogen gas to ammonia with the concomitant obligate production of hydrogen during the process of nitrogen fixation. This difficult reaction requires large amounts of ATP and reductant and, therefore, does not represent an efficient method of hydrogen production in terms of commercial utility (Simpson & Burris, "A Nitrogen Pressure of 50 Atmospheres Does Not Prevent Evolution of Hydrogen by Nitrogenase," *Science.* 224:1095-7 (1984)). However, a strategy to identify microbe strains, either naturally occurring or mutant forms, which have uncoupled hydrogen production from nitrogen fixation so that hydrogen production is metabolically advantageous to the growth and survival of the organism may represent a suitable means to develop a commercially efficient biocatalyst for hydrogen production.

The present invention is directed to achieving this objective.

SUMMARY OF THE INVENTION

One aspect of the present invention relates to a method of screening for microbial strains capable of generating hydrogen. The method includes inoculating a sample containing one or more microbes into a cell culture medium to form an inoculated culture medium. The inoculated culture medium is incubated under hydrogen producing conditions. Once incubating causes the inoculated culture medium to produce hydrogen, microbes in the inoculated culture medium are identified as candidate microbe strains capable of generating hydrogen.

Another aspect of the present invention relates to a method of producing hydrogen. This method includes providing a microbe strain in a culture medium under conditions in which the microbe strain is capable of producing hydrogen. The culture medium containing the microbe strain is incubated under conditions effective to produce hydrogen.

The present invention also relates to an isolated hydrogen producing microbe strain. This strain may contain one or more mutations within nucleic acid molecules of the wild-type form of the microbe strain encoding one or more regulatory proteins involved in hydrogen production The present invention, described to obtain and maintain bacteria for which hydrogen production is advantageous, can be useful in the context of a commercial process as it provides a selection strategy that can be applied to maintain continuous hydrogen production.

An analysis of strains of diverse species of photosynthetic bacteria using the present invention can reveal new hydrogen-producing enzymes, highlight the diversity of strategies that can be used by bacteria to regulate hydrogen production, and uncover new genes for enabling hydrogen-producing enzymes to function efficiently in whole cells.

BRIEF DESCRIPTION OF THE DRAWINGS

FIGS. 1A-B relate to hydrogen production by *Rhodopseudomonas palustris*.

FIGS. 3A-B illustrate gene expression analysis of the four isolated hydrogen-producing mutant strains.

DETAILED DESCRIPTION OF THE INVENTION

One aspect of the present invention relates to a method of screening for microbial strains capable of generating hydrogen. The method includes inoculating a sample containing one or more microbes into a cell culture medium to form an inoculated culture medium. The inoculated culture medium is incubated under hydrogen producing conditions. Once incubating causes the inoculated culture medium to produce hydrogen, microbes in the inoculated culture medium are identified as candidate microbe strains capable of generating hydrogen.

In some cases, the candidate microbe strain contained in the sample may grow in the hydrogen producing conditions without acquiring any mutation. In other cases, the candidate microbe strain contained in the sample may be unable to grow in the hydrogen producing conditions without acquiring one or more mutations. These mutants adapt a phenotype in which hydrogen production is metabolically required for the survival and growth of the organism under the screening conditions.

Candidate microbe strains may include anoxygenic photosynthetic bacteria. Genera of bacteria suitable for screening include, but are not limited to, *Rhodopseudomonas, Blastochloris, Rhodobacter, Rhodospirillum, Rubrivivax, Rhodomicrobium, Rhodoferax, and Rhodocyclus*. In a preferred embodiment of the invention, *Rhodopseudomonas*, a genus of purple non-sulfur, metabolically versatile bacteria found in many terrestrial and marine soil and water environments is utilized. Members of this genus include, but are not limited to, *R. cryptolactis, R. faecalis, R. julia, R. palustris,* and *R. rhenobacensis*.

When grown in light under anaerobic conditions, with organic compounds present, most anoxygenic photosynthetic bacteria generate ATP by cyclic photophosphorylation and use carbon compounds biosynthetically to make cell biomass. Carbon substrates that are electron-rich relative to cell material cannot be assimilated unless an external electron sink such as carbon dioxide, nitrate, or dimethyl sulfoxide is available to dissipate excess reducing equivalents (McEwan, "Photosynthetic Electron Transport and Anaerobic Metabolism in Purple Non-Sulfur Phototrophic Bacteria," *Antonie Van Leeuwenhoek*. 66:151-64 (1994), which is hereby incorporated by reference in its entirety). Alternatively, some cells dissipate excess reducing power via the production of hydrogen through nitrogen fixation (Joshi et al., "A Global Two Component Signal Transduction System that Integrates the Control of Photosynthesis, Carbon Dioxide Assimilation, and Nitrogen Fixation," *Proc. Natl. Acad. Sci. USA*. 93:14515-20 (1996), which is hereby incorporated by reference in its entirety). For these bacteria, non-nitrogen fixing conditions are unfavorable for survival presumably, because synthesis of nitrogenase is repressed, and, therefore, hydrogen production is also repressed. The strategy underlying the screening method described herein takes advantage of this finding.

Inoculating microbes into an environment which combines an electron-rich source of carbon with light energy under non-nitrogen fixing conditions will identify natural hydrogen producing strains and will force the mutagenesis of other strains to become hydrogen producing strains. Microbes which grow under the screening conditions described herein represent strains which have redirected metabolism to uncouple hydrogen production from nitrogen fixation and which utilize nitrogenase to produce hydrogen directly.

The sample containing one or more microbes is inoculated into a cell culture medium and incubated under anaerobic conditions, in the presence of light, in an electron-rich carbon containing culture medium under non-nitrogen fixing conditions. Sunlight provides an ideal energy source, however, other sources of energy include incandescent light bulbs or any other artificial sources of light. The source of nitrogen is preferably a reduced form or one that is capable of repressing nitrogenase activity. One such form of nitrogen is ammonium sulfate. Sources of electron-rich reduced carbon include, but are not limited to, cyclohexanecarboxylate, acetate, p-coumarate, succinate, ethanol, toluene, benzoate, butyrate, and butanol.

Once a hydrogen producing strain has been identified it can be isolated and utilized for the production of hydrogen. The method of producing hydrogen involves providing a microbe strain in culture medium under conditions in which the microbe strain is capable of producing hydrogen. The culture medium containing the microbe strain is incubated under conditions effective to produce hydrogen. Hydrogen production can occur under a variety of cultivation conditions in the absence of oxygen, nitrogen or other gases as long as light and an electron donor are supplied.

If the hydrogen producing microbe strain that has been identified is a mutant strain, said strain can be subjected to gene expression analysis to identify genes substantially involved in hydrogen production pathways. Such analysis can include standard nucleic acid amplification assays such as quantitative RT-PCR or PCR or hybridization based assays using oligonucleotide arrays such as those disclosed in U.S. Pat. No. 6,045,996 to Cronin et al., or U.S. Pat. No. 5,925,525 to Fodor et al., which are hereby incorporated by reference in their entirety. Additionally, hydrogen producing strains can also be subjected to genetic analysis and mapping using any standard DNA sequencing techniques known in the art to identify any possible mutations responsible for hydrogen production. Such methods of nucleic acid sequencing include the Sanger dideoxy method which utilizes enzymatic elongation procedures with chain terminating nucleotides as described in Sanger et al. *Proc. Natl. Acad. Sci. USA* 74:5463-5467 (1977) which is hereby incorporated by reference in its entirety, or the Maxam and Gilbert method which utilizes chemical reactions exhibiting specificity of reaction to generate nucleotide specific cleavages as described in Maxam et al., *Methods in Enzymology* 65:499-559 (1980) which is hereby incorporated by reference in its entirety. Additionally, the methods and apparatus for sequencing nucleic acids as disclosed in WO/92/010588 to Fodor et al, which is hereby incorporated by reference in its entirety, can also be used.

The hydrogen producing microbe strain may have increased hydrogenase activity, which for example, may result from an increase in hydrogenase gene expression. Likewise, the hydrogen producing microbe strain may have increased nitrogenase activity, which may result from an increase in nitrogenase gene expression. The hydrogen producing microbe strain may contain one or more mutations within nucleic acid molecules encoding one or more of the regulatory proteins involved in hydrogen production. Hydrogen producing microbe strains that have one or more mutations which directly or indirectly increase hydrogenase or nitrogenase activity are also contemplated. The molybdenum nitrogenase gene cluster represents one target of a network of regulatory proteins that is indirectly involved in hydrogen production and may be a preferred target for mutation. The hydrogen producing microbe strain may be *R. palustris* having one or more mutations occurring within the transcription activator protein NifA, comprising the amino acid sequence of SEQ ID NO:1, which is encoded by the nucleic acid sequence of SEQ ID NO:2. In particular, SEQ ID NO:1 is as follows:

```
Met Ala Gln Arg Glu Ile Arg Leu Val Asp Asn Glu Tyr Pro Ser Pro
1               5                   10                  15

Ser Met Thr His Pro Pro Ile Pro Leu Ser Asp Ile Ala Leu Thr Gly
            20                  25                  30

Ile Phe Glu Ile Ser Lys Ile Leu Thr Ser Pro Ala Arg Leu Glu Ile
        35                  40                  45

Thr Leu Ala Asn Val Val Asn Leu Leu Gln Ser Phe Leu Gln Met Arg
    50                  55              60

Asn Gly Val Val Ser Leu Leu Ala Asp Asp Gly Val Pro Asp Ile Thr
65              70                  75                      80

Val Gly Val Gly Trp Asn Glu Gly Ser Asp Asn Arg Tyr Arg Ala Arg
                85                  90                  95

Leu Pro Gln Lys Ala Ile Asp Gln Ile Val Ala Thr Ala Val Pro Leu
            100                 105                 110

Val Ala Asp Asn Val Ser Ala His Pro Met Phe Thr Ala Ala Asp Ala
        115                 120                 125

Met Ala Leu Gly Ala Thr Asp Glu Ile Arg Val Ser Phe Ile Gly Val
    130                 135                 140

Pro Ile Arg Ile Asp Ser Arg Val Val Gly Thr Leu Ser Ile Asp Arg
145                 150                 155                 160

Val Arg Asp Gly Arg Ser His She Arg Met Asp Ala Asp Val Arg Phe
                165                 170                 175

Leu Thr Met Val Ala Asn Leu Ile Gly Gin Thr Val Lys Leu His Arg
            180                 185                 190

Val Val Ala Arg Asp Arg Glu Arg Leu Met Ala Glu Ser His Arg Leu
        195                 200                 205

Gln Lys Glu Leu Ser Glu Leu Lys Pro Glu Arg Glu Arg Lys Arg Val
    210                 215                 220

Lys Val Asp Gly Ile Val Gly Glu Ser Pro Ala Ile Arg Lys Leu Leu
225                 230                 235                 240

Ala Lys Val Ser Ile Ile Ala Lys Ser Gln Ser Pro Val Leu Leu Arg
            245                 250                 255

Gly Glu Ser Gly Thr Gly Lys Glu Leu Ile Ala Lys Ala Ile His Glu
                260                 265                 270

Leu Ser Ala Arg Ala Asn Gly Pro Phe Ile Lys Ile Asn Cys Ala Ala
        275                 280                 285

Leu Pro Glu Ser Val Leu Glu Ser Glu Leu Phe Gly His Glu Lys Gly
    290                 295                 300

Ala She Thr Gly Ala Ile Ala Ser Arg Lys Gly Arg She Glu Leu Ala
305                 310                 315                 320

Asp Lys Gly Thr Leu Phe Leu Asp Glu Ile Gly Glu Ile Ser Ala Ser
            325                 330                 335

She Gln Ala Lys Leu Leu Arg Val Leu Gin Glu Gin Glu She Glu Arg
        340                 345                 350

Val Gly Gly Asn Gin Thr Ile Lys Val Asn Val Arg Ile Val Ala Ala
    355                 360                 365

Thr Asn Arg Asn Leu Glu Glu Ala Val Ala Arg Lys Glu She Arg Ala
370                 375                 380

Asp Leu Tyr Tyr Arg Ile Asn Val Val Pro Met Ile Leu Pro Pro Leu
```

-continued

```
                385                 390                 395                 400
Arg Asp Arg Pro Ser Asp Ile Pro Leu Leu Ala Ser Glu Phe Leu Lys
                405                 410                 415

Asn Phe Asn Lys Glu Asn Gly Arg Glu Leu Ala Phe Glu Ser His Ala
                420                 425                 430

Leu Asp Leu Leu Lys Ala Cys Ser Phe Pro Gly Asn Val Arg Glu Leu
                435                 440                 445

Glu Asn Cys Val Arg Arg Thr Ala Thr Leu Ala Met Gly Pro Glu Ile
    450                 455                 460

Arg Asp Ser Asp Phe Ala Cys His Gln Asp Glu Cys Leu Ser Ala Ile
465                 470                 475                 480

Leu Trp Lys Gly His Ala Glu Pro Ala Pro Glu Arg Pro Arg Pro Glu
                485                 490                 495

Ile Pro Leu Gln Val Leu Pro Arg Lys Ala Pro Val Glu Ile Val His
                500                 505                 510

Pro Arg Glu Pro Val Ala Ser Ala Asp Asp Phe Ala Pro Ala Pro Val
                515                 520                 525

Arg Ser Glu Met Pro Ser Asp Glu Ser Asn Met Ser Glu Arg Glu Arg
    530                 535                 540

Leu Ile Asn Ala Met Glu Arg Ala Gly Trp Val Gln Ala Lys Ala Ala
545                 550                 555                 560

Arg Ile Leu Gly Leu Thr Pro Arg Gln Ile Gly Tyr Ala Leu Lys Lys
                565                 570                 575

His Asn Ile Glu Leu Lys His Phe
                580
```

SEQ ID NO:2 is as follows:

```
atggctcagc gcgaaattcg ccttgtcgat aacgagtacc cgtcgccttc gatgacccat    60
cctccgatac cgctgagtga catcgcgctc accggcattt tcgagatctc gaaaatcctc   120
acctcaccgg cgcggttgga gatcaccctc gccaacgtcg tcaacctgct gcagtcattt   180
ttgcagatgc gcaacggcgt ggtgtcgctg ctcgccgatg acggcgtgcc cgatattacc   240
gtcgggtcg gctggaatga ggggagcgat aaccgctatc gcgcccggct gccgcagaag   300
gcgatcgacc agatcgtcgc gaccgcggtg ccgctggtcg ccgacaacgt ctccgcccac   360
ccgatgttca ccgcggccga cgctatggcg ctcggcgcaa ctgacgaaat ccgggtgtcg   420
ttcatcggcg tgccgatccg gatcgactcg cgggtggtgg ggacgctgag catcgaccgc   480
gtccgcgatg gccgttcgca cttccggatg gacgccgacg tgcgcttcct caccatggtg   540
gccaatctga tcggccaaac cgtgaagctg caccgcgtcg tcgcccgcga ccgcgagcgg   600
ctgatggcga aaagccaccg gctgcagaag gaactgtccg agctgaagcc ggagcgcgag   660
cgtaagcggg tcaaggtcga cggcatcgtc ggcgagagcc cggcgatccg caaattgctg   720
gccaaggtca gcatcatcgc caagtcgcag tcgcccgtgt tgctgcgcgg cgagtcggga   780
accggcaagg agctgatcgc aaaagcgatc cacgaattgt cggcgcgcgc caacggcccg   840
ttcatcaaga tcaactgcgc ggcgctgccg aatcggtgc tggagtccga gctgttcggg   900
cacgagaagg gcgccttcac cggcgcgatc gcctcgcgca agggccggtt cgagctggcc   960
gacaagggca cgctgttttct cgacgagatc ggtgagatct ccgcgtcgtt ccaggccaag  1020
ctgctgcgcg tcttgcagga gcaggaattc gaacgggtcg gcggcaacca gaccatcaag  1080
gtcaatgtcc ggatcgtcgc cgccaccaac cgcaatctgg aagaggcagt ggcgcgcaag  1140
gaattccgcg ccgatctgta ttaccgcatc aatgtagtgc cgatgatcct gccgccgctg  1200
```

```
cgcgaccggc ccagcgacat cccgctgctg gcgagcgaat tcctgaagaa cttcaacaag   1260
gagaacggcc gcgagctggc cttcgagtcg cacgcgctgg atctgctgaa ggcctgctcg   1320
ttccccggca acgtccgcga gctggagaac tgcgtgcgcc gcaccgcgac cctggcgatg   1380
gggccggaaa tccgcgacag cgatttcgcc tgtcaccagg acgaatgcct gtcggcgatc   1440
ctgtggaagg gtcacgccga acctgcgccc gagcgcccac gccctgagat cccgttgcag   1500
gtcctgccgc gcaaggcgcc ggtggaaatc gtccatccgc gcgagccggt cgcatcagcg   1560
gatgattttg cgccggcgcc ggttcgttcc gagatgccat ccgacgaatc gaacatgtcg   1620
gagcgcgagc ggctgatcaa cgccatggag cgagccgggt gggtgcaggc gaaggccgca   1680
cgcattctcg gcctcacgcc gcgccagatc ggctacgcgc tgaagaagca caacatcgag   1740
ctcaagcact tctga                                                   1755
```

NifA is an RNA polymerase sigma 54-dependant transcriptional activator that is required for nitrogenase gene expression in R. palustris. Preferably, the amino acid mutations in NifA promote a conformational change in the protein, rendering it competent to activate gene expression constitutively. Because NifA regulates nitrogenase activity, preferable mutations promote a conformational change consistent with rendering the protein competent to activate nitrogenase gene expression constitutively. Individual amino acid mutations within the amino acid sequence of SEQ ID NO: 1 which are suitable for increasing nitrogenase gene expression and activity include, for example, a glutamine to proline substitution at amino acid 209 ($Q^{209} \rightarrow P$), a methionine to lysine substitution at amino acid 202 ($M^{202} \rightarrow K$), a leucine to arginine substitution at amino acid 212 ($L^{212} \rightarrow R$), a serine to proline substitution at amino acid 213 ($S^{213} \rightarrow P$), and combinations thereof.

In addition to the molybdenum nitrogenase gene cluster, bacteria such as R. palustris, encode other nitrogenases, such as vanadium and iron nitrogenases, that may be capable of facilitating hydrogen production (Larimer, et al., "Complete Genome Sequence of the Metabolically Versatile Photosynthetic Bacterium Rhodopseuciamonas palustris," Nat. Biatechnol. 22:55-61 (2004), which is hereby incorporated by reference in its entirety). Alternative nitrogenase synthesis depends on many of the cofactor and assembly proteins encoded by the nif gene cluster (Oda, et al., "Functional Genomic Analysis of Three Nitrogenase Isozymes in the Photosynthetic Bacterium Rhadopseudamonas palustris," J. Bacterial. 187:7784-94 (2005), which is hereby incorporated by reference in its entirety). Thus, it is possible that a second mutation within the nif gene cluster in addition to a NifA mutation may promote constitutive synthesis of anf and vnf genes for alternative nitrogenase production. Likewise, mutations within the vanadium nitrogenase and iron nitrogenase gene clusters that directly or indirectly result in the constitutive expression of one or both of these enzymes, alone or in combination with the molybdenum nitrogenase are also contemplated.

Amino acid mutations which influence the expression or activity of genes indirectly affecting nitrogenase activity are also contemplated. Such genes include those involved in the conversion of light to ATP such as (gene numbers given before the parenthetical and location on the chromosome given in parentheses) RPA3012-3013 (3410110-3410457), RPA1505-1554 (1671137-1725322), RPA2653-2654 (3017745-3018093), RPA4291-4292 (4838558-4838926) and RPA149'-1492 (1655417-1655764) in R. palustris (the GenBank/EMBL/DDBJ accession number of the R. palustris CGA009 genome is BX571963). Additionally, genes encoding proteins involved in channeling electrons to nitrogenase such as R. palustris genes, RPA1928 (2162133-2163041), RPA4602-4605 (5188040-5191666), RPA4612 (5197263-5197574), RPA4629 (5209974-5210195), and RPA4631 (5211934-5212128); genes involved in supplying iron required for enzyme function such as R. palustris genes RPA2380-2391 (2697057-2711837); and genes involved in supplying other transition metal ions such as molybdenum for enzymes function, including the R. palustris gene RPA0148 (166873-167409) are also contemplated. The complete genome sequence of R. palustris has been described in Larimer, et al., "Complete Genome Sequence of the Metabolically Versatile Photosynthetic Bacterium Rhodopseudomonas palustris," Nature Biotechnology. 22(1):55-61 (2004), which is hereby incorporated by reference in its entirety.

Once amino acid mutations rendering a microbe strain competent of constitutive hydrogen production have been identified through genetic sequencing, customary cloning techniques known in the art can be utilized to construct recombinant strains. The microbe strain capable of producing hydrogen can be a recombinant strain containing one or more mutations within nucleic acid molecules of the wild-type form of the microbe strain as described above.

The present invention also relates to an isolated hydrogen producing microbe. This strain may contain one or more mutations within nucleic acid molecules of the wild-type form of the microbe strain which encode for one or more regulatory proteins involved in hydrogen production. The isolated hydrogen producing microbe strain may have one or more mutations that increase hydrogenase activity. Likewise, the isolated hydrogen producing microbe strain may have one or more mutations that increase nitrogenase activity. Other characteristics of such microbes are described above.

EXAMPLES

The Examples set forth below are for illustrative purposes only and are not intended to limit, in any way, the scope of the present invention.

Example 1

Bacterial Strains and Growth Conditions

The bacterial strains and plasmids used are listed in Table 1.

TABLE 1

Strains, Plasmids and Primers

| Strain, plasmid, or primer | Genotype or phenotype[a] | Reference, origin, or description |
|---|---|---|
| *R. palustris* strains | | |
| CGA009 | Wild type strain; spontaneous Cm[R] derivative of CGA001 | 1 |
| CGA570 | Spontaneous mutant able to grow with cyclohexanecarboxylate in the presence of ammonium sulfate (NifA S213P) | CGA009, this study |
| CGA571 | Spontaneous mutant able to grow with cyclohexanecarboxylate in the presence of ammonium sulfate (NifA Q209P) | CGA009, this study |
| CGA572 | Spontaneous mutant able to grow with cyclohexanecarboxylate in the presence of ammonium sulfate (NifA, L212R) | CGA009, this study |
| CGA574 | Spontaneous mutant able to grow with cyclohexanecarboxylate in the presence of ammonium sulfate (NifA M202K) | CGA009, this study |
| CGA757 | ΔnifA, 1332 bp deleted | 7 CGA009, this study |
| CGA581 | nifA* (Q209P) | CGA757, this study |
| CGA584 | nifA* (M202K) | CGA757, this study |
| *E. coli* strains | | |
| DH5α | Fλ' recA1Δ(lacZYA-argF)U169hsdR17thi-1gyrA96 supE44 endA1relA1 φ80lacZΔM15 | GIBCO-BRL |
| S17-1 | thi pro hds R hdsM⁻ recA; chromosomal insertion of RP4-2 (Tc::MuKm::Tn7) | 2 |
| Plasmids | | |
| pJQ200KS | Gm[R], sacB, mobilizable suicide vector | 3 |
| pUC19 | Ap[R], high-copy number cloning vector | 4 |
| puC19-nifA*571 | Ap[R], 3 kb fragment containing a nifA gene and flanking regions from CGA571 amplified by PCR and cloned into XbaI sites of pUC19 | This study |
| PJQ200KS-nifA*571 | Gm[R], 3 kb fragment containing a nifA gene and flanking regions from CGA571 amplified by PCR and cloned into XbaI sites of pJQ200KS | This study |
| | Genotype, phenotype, or sequence of primer[a] (5' to 3') | |
| pUC19-nifA*574 | Ap[R], 3-kb fragment containing a nifA mutant gene and flanking regions from CGA574 amplified by PCR and cloned into XbaI sites of pUC19 | This study |
| PJQ200KS-nifA *574 | Gm[R], 3-kb fragment containing a nifA mutant gene and flanking regions from CGA574 amplified by PCR and cloned into XbaI sites of pJQ200KS | This study |

[a]Gm[R], gentamicin resistance; Ap[R], ampicillin resistance; Cm, chloramphenicol resistance
([1]Larimer, et al., "Complete Genome Sequence of the Metabolically Versatile Photosynthetic Bacterium *Rhodopseudomona palustris*." *Nat. Biotechnol.* 22: 55-61 (2004);
[2]Simon, et al., "A Broad Host Range Mobilization System for in vivo Genetic Engineering: Transposon Mutagenesis in Gram-Negative Bacteria," *Bio/Technology*. 1: 784-91 (1983);
[3]Quandt & Hynes, "Versatile Suicide Vectors Which Allow Direct Selection for Gene Replacement in Gram-Negative Bacteria," *Gene*. 127: 15-21 (1993);
[4]Yanisch-Perron, et al., "Improved M13 Phage Cloning Vectors and Host Strains; Nucleotide Sequences of the M13mp18 and pUC19 Vectors," *Gene*. 33: 103-19 (1985), which are hereby incorporated by reference in their entirety).

All work was carried out with the *R. palustris* wild type strain CGA009 or its derivatives. Strain CGA009 is defective in uptake hydrogenase activity (Rey, et al., "Regulation of Uptake Hydrogenase and Effects of Hydrogen Utilization on Gene Expression in *Rhodopseudomonas palustris*," *J. Bacteriol.* 188:6143-52 (2006), which is hereby incorporated by reference in its entirety). *R. palustris* was grown and manipulated aerobically in defined mineral medium containing 10 mM succinate as a carbon and energy source and a 100 µg per ml gentamicin (Gm) (Kim et al. "Regulation of Benzoate-CoA Ligase in *Rhodopseudomonas palustris*," *FEMS Microbiol. Lett.* 83:199-204 (1991), which is hereby incorporated by reference in its entirety). Otherwise *R. palustris* strains were grown in defined medium anaerobically with light in sealed tubes containing argon gas in the headspace and $(NH_4)_2SO_4$ supplied as a nitrogen source (non-nitrogen-fixing conditions) or with a nitrogen gas headspace and $(NH_4)_2SO_4$ omitted (nitrogen-fixing conditions). Carbon sources included succinate (10 mM), acetate (20 mM), p-coumarate (4.5 mM), or cyclohexanecarboxylate (5.7 mM). *Escherichia coli* strains DH5α and S17-1 were grown at 37° C. in Luria-Bertani (LB) medium. Where indicated, *R. palustris* was grown with 100 µg per ml gentamicin (Gm). *E. coli* was grown with 100 µg per ml ampicillin, or 20 µg per ml Gm.

Example 2

Strain Constructions

DNA fragments (~3 kb) spanning nifA plus flanking regions from CGA571 and CGA574 were generated by PCR. The amplification products contained engineered XbaI cloning sites at both ends. These products were digested with XbaI and cloned into XbaI-digested pUC19 to generate pUC19-nifA*571, and pUC19-nifA*574. The Xba-I fragments were then cloned into pJQ200KS to generate pJQ200KS-nifA*571, and pJQ200KS-nifA*574. These constructs were mobilized from *E. coli* S17-1 into *R. palustris* CGA757 (ΔnifA, this strain cannot grow under nitrogen-fixing conditions) by conjugation. Colonies that contained plasmids that had undergone a single recombination to become inserted into the chromosome were identified by growth on PM plus Gm. These colonies were spread onto nitrogen-fixing agar medium supplemented with 10% sucrose and incubated anaerobically in order to select for strains that had undergone a double recombination to lose the sacB-containing vector. Gene replacements were confirmed by PCR and sequencing.

Example 3

Description of the *R. Palustris* Genechip

*R. palustris* custom designed GeneChip was manufactured by Affymetrix (Santa Clara, Calif.) with the following specifications: 99.8% of *R. palustris* predicted open reading frames genes were represented by unique probe sets (16 probe pairs and their corresponding mismatch for each). In addition, the GeneChip contains information for all intergenic regions larger than 150 bp.

Example 4

DNA Microarray Experiments

RNA was isolated as previously described (Oda, et al., "Functional Genomic Analysis of Three Nitrogenase Isozymes in the Photosynthetic Bacterium *Rhadopseudomonas palustris*," *J. Bacterial.* 187:7784-94 (2005), which is hereby incorporated by reference in its entirety). cDNA was synthesized from 10 µg of purified RNA, with semirandom hexamer primers having an average G+C content of 75%, and Superscript II reverse transcriptase (Life Technologies, Carlsbad, Calif.). Fragmentation and labeling were performed according to the manufacturer's recommendations (Affymetrix). Samples were hybridized and scanned at the Center for Expression Arrays, University of Washington according to specifications provided by the manufacturer. The expression profiles were analyzed as previously described (Schuster, et al., "Identification, Timing, and Signal Specificity of *Pseudomonas aeruginosa* Quorum-Controlled Genes: A Transcriptome Analysis," *J. Bacterial.* 18:2066-79 (2003), which is hereby incorporated by reference in its entirety).

Example 5

Nitrogenase Activity and Hydrogen Measurements

Nitrogenase activity was measured by the acetylene reduction assay as described previously (Oda, et al., "Functional Genomic Analysis of Three Nitrogenase Isozymes in the Photosynthetic Bacterium *Rhodopseudomonas palustris*," *J. Bacterial.* 187:7784-94 (2005), which is hereby incorporated by reference in its entirety). Hydrogen production was measured using a Hewlett Packard 5890 series II gas chromatograph equipped with a thermal conductivity detector and molecular sieve-13× column (80/100 mesh, I.D. ¼ in. by 8 ft) (Oda, et al., "Functional Genomic Analysis of Three Nitrogenase Isozymes in the Photosynthetic Bacterium *Rhodopseudomonas palustris*," *J. Bacteriol.* 187:7784-94 (2005), which is hereby incorporated by reference in its entirety). Protein concentrations were determined using the Bio-Rad (Richmond, Calif.) protein assay kit.

Example 6

Gene Sequencing

In order to identify the mutation(s) responsible for the hydrogen-producing phenotype, nifA and its promoter region, glnK1, draT1, draT2, draG, were sequenced in all strains. In addition, regS, regR, cbbR, glnB, glnK2, in CGA570 and ntrB, ntrC, glnK2, vnfA, anfA in CGA572 were also sequenced. All mutations identified map to the regulatory protein NifA.

Figure 1A:
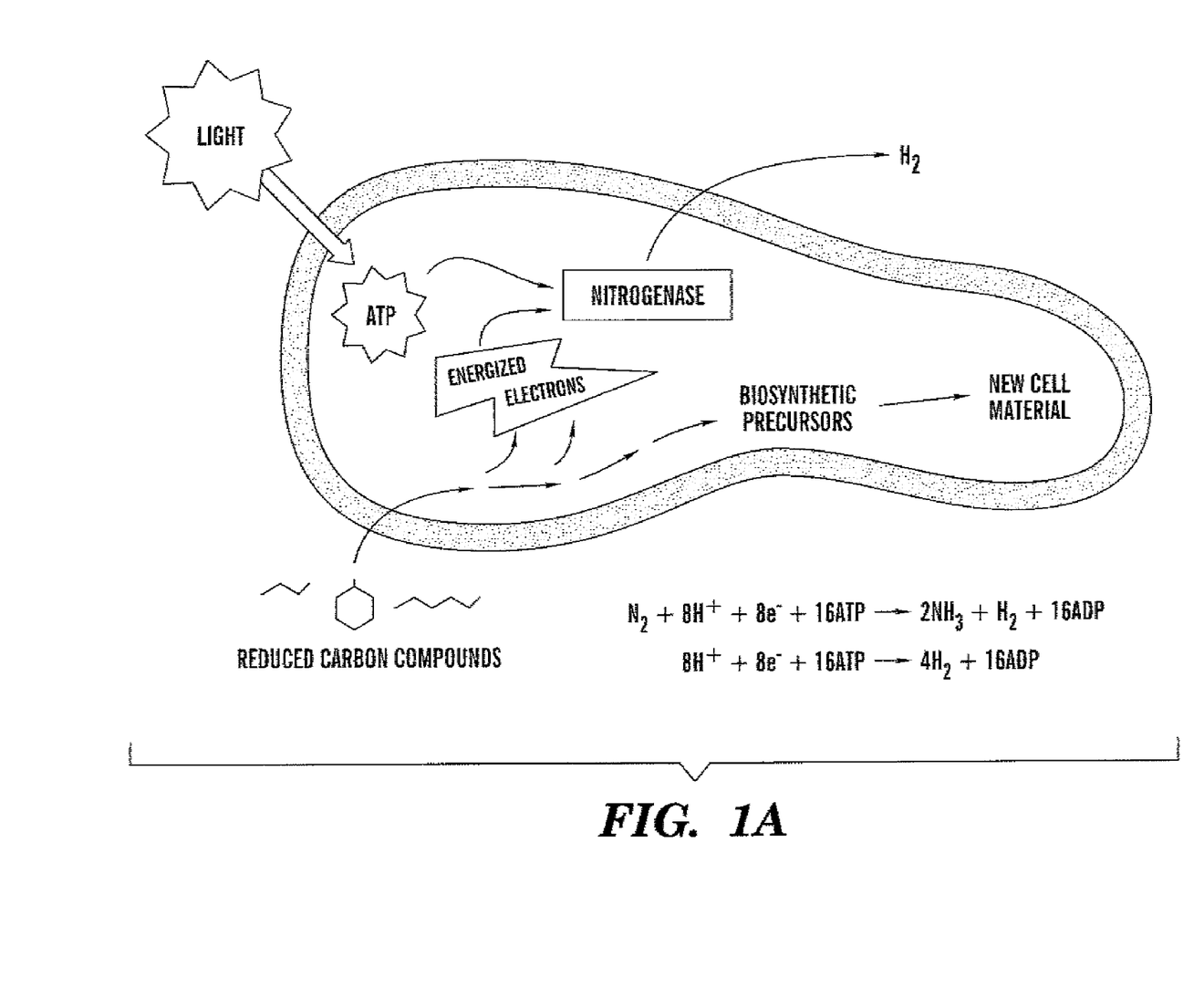
FIG. 1A shows the metabolic route leading to biohydrogen production by *R. palustris* strain CGA009. Carbon sources that are electron-rich (highly reduced) relative to cell material can be degraded and used to support cell growth only if cells are able to produce hydrogen via nitrogenase. The theoretical stoichiometries for nitrogenase reactions for hydrogen production in the presence and absence of nitrogen gas are indicated.
Figure 1B:
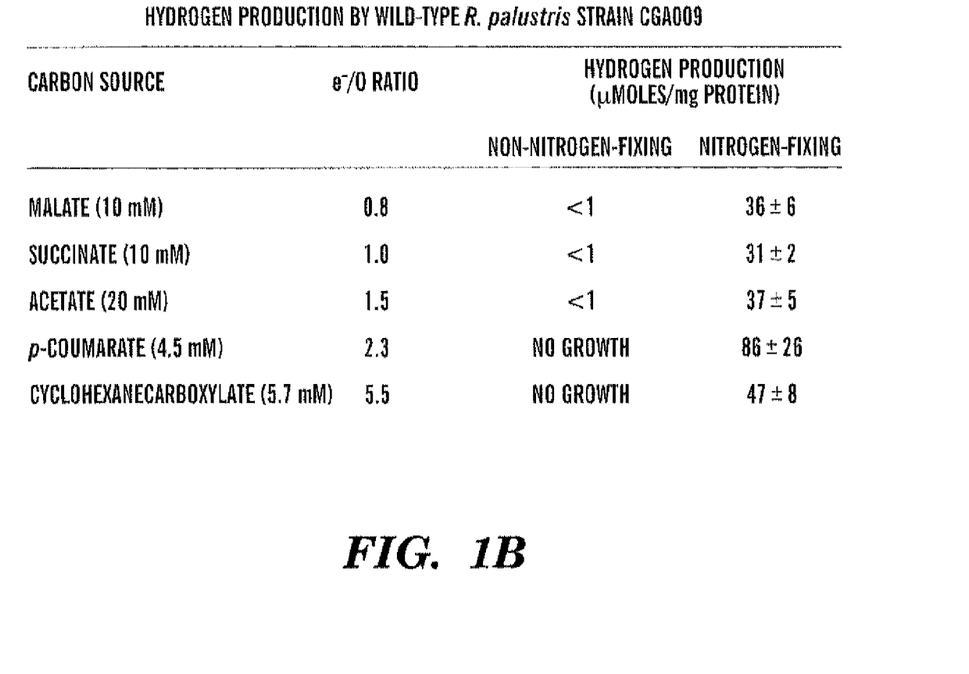
FIG. 1B shows hydrogen production by wild-type *R. palustris* strain CGA009. The $e^-/O$ ratio represents the ratio of the number of hydrogen atoms to the number of oxygen atoms in the carbon source. Data were acquired from exponentially growing cultures (optical density at 660, 0.2 to 0.5). Values are the average of three or more measurements with standard deviations indicated.

When grown in light with organic compounds present, anoxygenic photosynthetic bacteria generate ATP by cyclic photophosphorylation and use carbon compounds biosynthetically to make cell biomass. Carbon substrates that are electron-rich relative to cell material cannot be assimilated unless an external electron sink, such as carbon dioxide, nitrate, or dimethyl sulfoxide, is available to dissipate excess reducing equivalents. Another process by which some cells dissipate excess reducing power is nitrogen fixation. Consistent with this, *R. palustris* grew on the electron-rich carbon compound cyclohexanecarboxylate if it was able to generate hydrogen as part of the process of nitrogen fixation (FIG. 1A). However, wild-type *R. palustris* failed to grow when incubated with cyclohexanecarboxylate or other reduced carbon compounds under non-nitrogen-fixing conditions, presumably because ammonium sulfate present in the growth medium repressed the synthesis of nitrogenase and therefore, hydrogen production (FIG. 1B). This observation suggested that mutant strains selected for growth on cyclohexanecarboxylate in the presence of ammonium would produce hydrogen constitutively. Inoculation of *R. palustris* wild-type cells in anaerobic culture tubes containing mineral medium with cyclohexanecarboxylate as a source of carbon, ammonium sulfate as the source of nitrogen, and light as the source of energy followed by several months of incubation resulted in growth of four mutant strains that were subsequently isolated and purified (Table 2).

TABLE 2

Doubling times of *R. palustris* wild type and hydrogen-producing mutants in the presence of ammonium[a]

| Strain | Doubling time[b] | |
|---|---|---|
| | acetate | cyclohexanecarboxylate |
| CGA009 | 8 ± 1 | no growth |
| CGA570 | 8 ± 1 | 15 ± 3 |
| CGA571 | 29 ± 4 | 28 ± 3 |
| CGA572 | 11 ± 2 | 22 ± 3 |
| CGA574 | 10 ± 2 | 18 ± 1 |

[a]Data are averages of at least three independent measurements, plus or minus standard deviation.
[b]Doubling times in hours.

Figure 2:
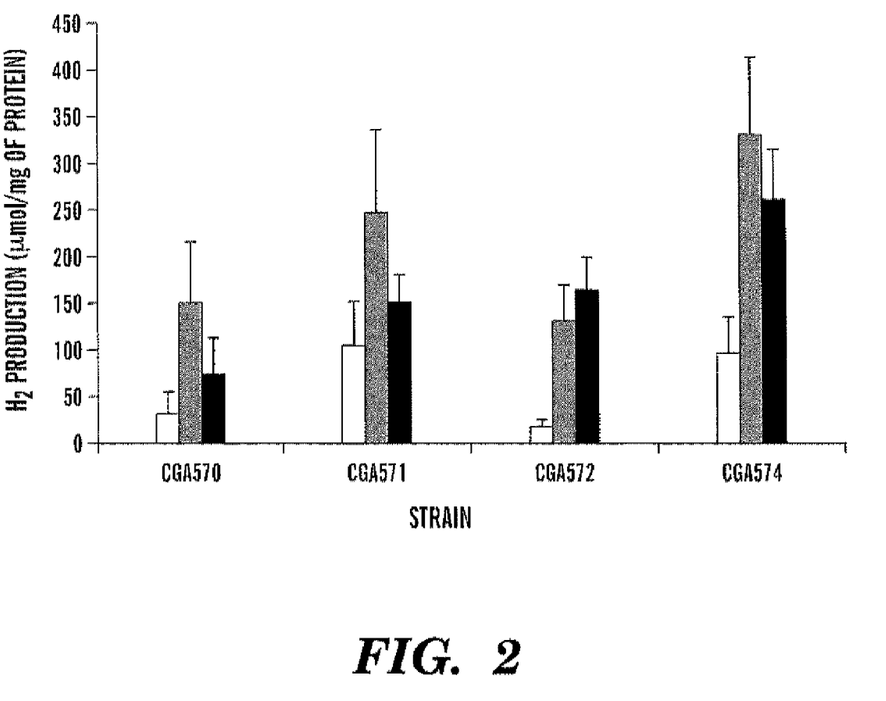
FIG. 2 shows hydrogen production by the four *R. palustris* mutant strains under non-nitrogen-fixing conditions. Data were acquired from exponentially growing cultures (optical density at 660, 0.2 to 0.5). □ Acetate, ▨ p-coumarate, and ■ cyclo-hexanecarboxylate. Values are the average of three or more measurements. Error bars show the standard deviation between repeat experiments. Concentrations of carbon sources are as in FIG. 1B.

Each of the four mutant strains produced hydrogen from renewable carbon compounds including acetate and p-coumarate, a plant lignin monomer, and cyclohexanecarboxylate, as depicted in FIG. 2, under the same conditions in which wild-type cells did not produce hydrogen (FIG. 1B). Each of the mutants had nitrogenase activity under all conditions (Table 3).

TABLE 3

Nitrogenase activity of *R. palustris* wild-type and hydrogen-producing mutants[a]

| Strain | Nitrogenase activity[b] | |
|---|---|---|
| | Non-nitrogen-fixing | Nitrogen-fixing |
| CGA009 | <1 | 112 ± 25 |
| CGA570 | 82 ± 25 | 144 ± 25 |
| CGA571 | 46 ± 7 | 54 ± 20 |
| CGA572 | 5 ± 2 | 59 ± 21 |
| CGA574 | 62 ± 47 | 92 ± 11 |

[a]Data are averages of at least three independent measurements, plus or minus standard deviation.
[b]Nitrogenase activity in nmol $C_2H_4$ formed/min/mg protein. Cells were grown with 20 mM acetate.

Because the mutants were not supplied with nitrogen gas during growth, it is hypothesized that nitrogenase catalyzed the synthesis of hydrogen without accompanying ammonia production. Many reports have shown that hydrogen is the only product formed by nitrogenase in the absence of nitrogen gas. Apparently, these mutant strains had overcome the regulatory barriers that prevent nitrogenase gene expression.

Figure 3A:
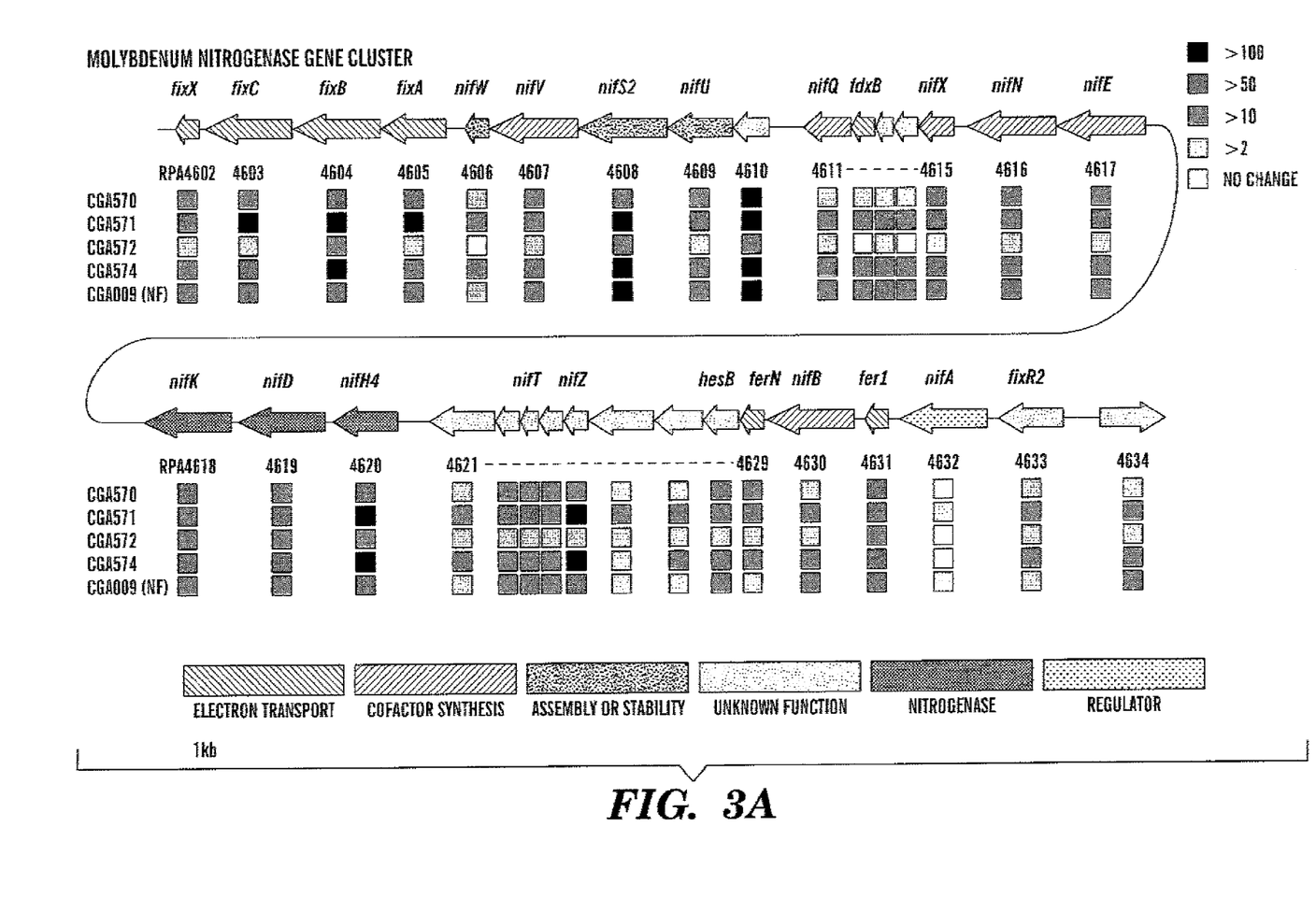
FIG. 3A shows the relative increase in the expression of genes in the molybdenum nitrogenase gene cluster in the hydrogen-producing strains of *R. palustris*.

Transcriptome analysis using the *R. palustris* custom GeneChip identified that the structural genes nifHDK, encoding the two subunits of molybdenum nitrogenase, were among the genes most highly expressed in the hydrogen-producing strains. Most of the 30 genes that surround nifHDK on the *R. palustris* chromosome were also expressed at high levels in the mutant strains (FIG. 3A). Many of these are homologous to genes in other bacteria shown to be involved in the synthesis and assembly of two complex metalloclusters that are part of the nitrogenase (Rubio & Ludden, "Maturation of Nitrogenase: A Biochemical Puzzle," *J. Bacterial.* 187:405-14 (2005), which is hereby incorporated by reference in its entirety).

Figure 3B:
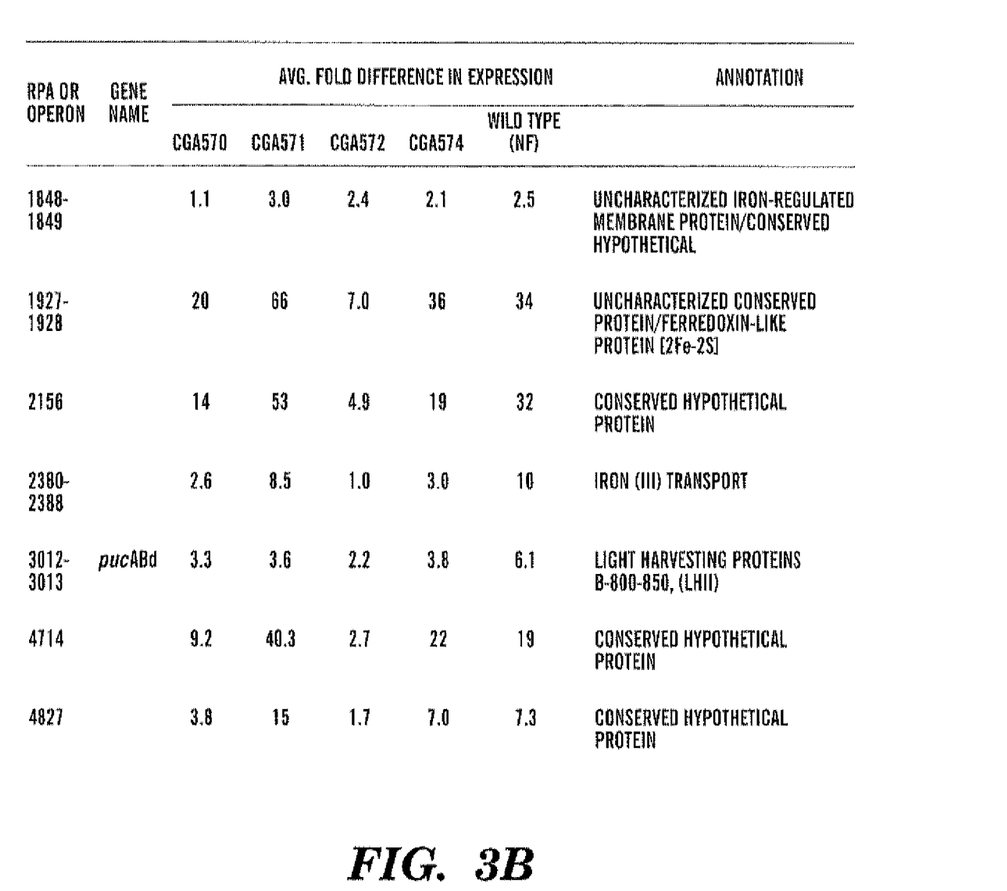
FIG. 3B lists the genes outside the nitrogenase gene cluster whose expression was increased in the hydrogen-producing strains of *R. palustris*. Cells were grown anaerobically in light with acetate under non-nitrogen-fixing conditions. The fold difference in gene expression is relative to wild type strains grown anaerobically in light with acetate and ammonium sulfate (non-nitrogen-fixing conditions). Gene expression in wildtype strains grown under nitrogen-fixing (NF) conditions is shown for comparison.

Normally, cells produce hydrogen as an unintended consequence of nitrogen fixation during ammonia deprivation, an environmental cue that alters the expression level of about 4% of the genome (Oda, et al., "Functional Genomic Analysis of Three Nitrogenase Isozymes in the Photosynthetic Bacterium Rhadopseudomonas palustris," *J. Bacterial.* 187:7784-94 (2005), which is hereby incorporated by reference in its entirety). Transcriptome analysis of the hydrogen-producing strains allows for the identification of genes that might be important for hydrogen production, as opposed to adaptation to ammonium starvation. Only 21 genes that are physically distant from the molybdenum nitrogenase cluster showed increased expression in at least three of the hydrogen-producing mutant strains compared to wild type. A subset of 18 of these genes also had increased expression levels in the wild type under nitrogen-fixing (and hydrogen-producing) conditions (FIG. 3B). Some of these likely encode proteins that indirectly facilitate nitrogenase activity, for example by supplying iron needed for enzyme function (RPA2380-2388). Of more direct relevance to hydrogen production are genes that enhance the ability of *R. palustris* to convert light to ATP or that are involved in efficient channeling to nitrogenase of electrons required for the reduction of protons into molecular hydrogen. RPA3012-3013 encode light harvesting II polypeptides that function to absorb light energy and transfer it to the bacteriochlorophyll-containing reaction center where it is converted into a proton gradient that is used to generate ATP (Scheuring, et al., "The Photosynthetic Apparatus of *Rhodopseudomonas palustris*: Structures and Organization," *J. Mol. Biol.* 358:83-96 (2006); Larimer, et al., "Complete Genome Sequence of the Metabolically Versatile Photosynthetic Bacterium *Rhodopseudomonas palustris*," *Nat. Biotechnol.* 22:55-61 (2004), which are hereby incorporated by reference in their entirety). RPA1928 codes for a ferredoxin predicted to function as an electron carrier. It may act in concert with the RPA1927 protein in this capacity. Electron transfer can be rate limiting for nitrogenase activity (Jeong et al., "Enhanced Nitrogenase Activity in Strains of *Rhodobacter capsulatus* that Overexpress the rnfGenes,"*J. Bacterial.* 182:1208-14 (2000), which is hereby incorporated by reference in its entirety). The intracellular pathways of transfer from electron donating substrate to the nitrogenase have not yet been studied in *R. palustris* but bear investigation as, in addition to RPA1928, four other ferredoxin genes, all in the nitrogenase gene cluster, are expressed at high levels in the hydrogen producing strains. Understanding the individual roles of these ferredoxins in transfer of electrons to nitrogenase will be important for developing a complete understanding of the route to hydrogen production from electron donating organic compounds in whole cells. In addition to genes of known or suspected function, the hydrogen-producing *R. palustris* strains expressed several genes (RPA2156, RPA4714 and RPA4827) of unknown function to high levels.

Figure 4:
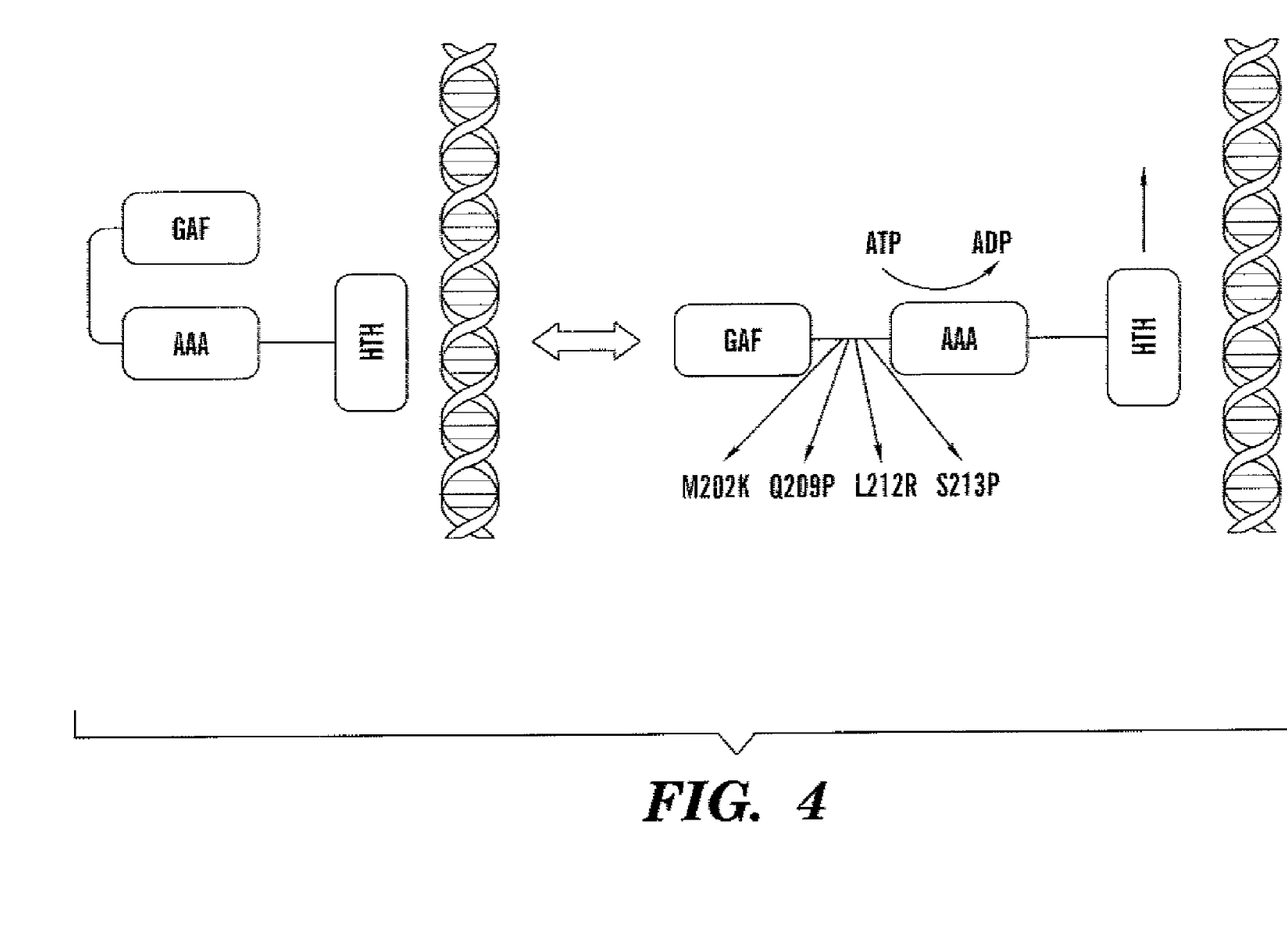
FIG. 4 illustrates the proposed effect of nifA mutations on transcriptional activation. The mutations are S213P for strain CGA570, Q209P for strain CGA571, L212R for strain CGA572, and M202K for strain. CGA574. A proposed configuration for NifA under non-inducing conditions is shown on the left. The four mutations indicated in the linker region may cause NifA to assume a conformation that mimics the active protein, as shown on the right.

The *R. palustris* genome encodes for a set of regulatory proteins that overlap with those in other bacteria known to control nitrogen fixation in response to intracellular nitrogen status (Oda, et al., "Functional Genomic Analysis of Three Nitrogenase isozymes in the Photosynthetic Bacterium *Rhodopseudomonas palustris*," *J. Bacterial,* 187:7784-94 (2005); Larimer, et al., "Complete Genome Sequence of the Metabolically Versatile Photosynthetic Bacterium *Rhodopseudomonas palustris*," *Nat. Biotechnol.* 22:55-61 (2004); Dixon et al., "Genetic Regulation of Biological Nitrogen Fixation," *Nat. Rev. Microbiol.* 2:621-31 (2004); Masepohl, et al., "Regulation of Nitrogen Fixation in the Phototrophic Purple Bacterium *Rhodobacter capsulatus*," *Mol. Microbial. Biotechnol.* 4:243-248 (2002); Zhang, et al., "Functional Characterization of Three GlnB Homologs in the Photosynthetic Bacterium *Rhodospirillum rubrum*: Roles in Sensing Ammonium and Energy Status," *J. Bacteriol.* 183: 6159-68 (2001); Zhang, et al., "GlnD is Essential for NifA Activation, NtrB/NtrC-Regulated Gene Expression, and Posttranslational Regulation of Nitrogenase Activity in the Photosynthetic, Nitrogen-Fixing Bacterium, *Rhodospirillum rubrum*," *J. Bacteriol.* 187:1254-65 (2005), which are hereby incorporated by reference in their entirety). To identify the mutations responsible for constitutive hydrogen production, genes predicted to be involved in these regulatory networks were sequenced (Oda, et al., "Functional Genomic Analysis of Three Nitrogenase Isozymes in the Photosynthetic Bacterium *Rhodopseudomonas palustris*," *J. Bacterial.* 187:7784-94 (2005); Dixon et al., "Genetic Regulation of Biological Nitrogen Fixation," *Nat. Rev. Microbiol.* 2:621-31 (2004), which are hereby incorporated by reference in their entirety). Four different single point mutations were identified in the regulatory gene nifA in the four hydrogen-producing strains (FIG. 4). NifA is an RNA polymerase sigma 54-dependant transcriptional activator that is required for nitrogenase gene expression in *R. palustris*. It contains a predicted central $AAA^+$ ATPase motif, a carboxy-terminal DNA binding domain, and an amino-terminal GAF domain. The sigma 54-interaction domain is in the central portion of the protein and overlaps the $AAA^+$ motif. GAF domains of NifA proteins from other bacteria sense nitrogen status directly as well as through interactions with other proteins (Little et al., "The Amino-Terminal GAF Domain of *Azotobacter vinelandii* NifA Binds 2-Oxoglutarate to Resist Inhibition by NifL Under Nitrogen-Limiting Conditions,"*J. Biol. Chem.* 278: 28711-8 (2003); Martinez-Argudo, et al., "Role of the Amino-Terminal GAF Domain of the NifA Activator in Controlling the Response to the Antiactivator Protein NifL," *Mol. Microbial.* 52:1731-44 (2004); Chen, et al., "Functional Analysis of the GAF Domain of NifA in *Azospirillum brasilense*: Effects of Tyr→Phe Mutations on NifA and its Interaction with GlnB," *Mol. Genet. Genomics.* 273:415-22 (2005), which are hereby incorporated by reference in their entirety). In proteins related to NifA, the amino-terminal domains modulate ATPase activity (Martinez-Argudo, et al., "Role of the Amino-Terminal GAF Domain of the NifA Activator in Controlling the Response to the Antiactivator Protein NifL," *Mol. Microbiol.* 52:1731-44 (2004); Studholme et al., "Domain Architectures of Sigma54-Dependent Transcriptional Activators," *J. Bacterial,* 185:1757-67 (2003); D'Autreaux, et al., "A Non-Haem Iron Centre in the Transcription Factor N or R Senses Nitric Oxide," *Nature.* 437: 769-72 (2005), which are hereby incorporated by reference in their entirety).

All mutations identified localized to the linker region between the regulatory domain and the AAA-domain (FIG. 4). It is likely that these mutations cause structural changes in NifA that relieve a repressive effect of the GAF domain on the AAA-ATPase domain, rendering the protein competent to activate gene expression constitutively. The genes that were expressed at elevated levels in the hydrogen-producing mutants (FIG. 3B), are a subset of the NifA regulon, which includes more than 120 genes. This suggests that the nifA mutations selected render this regulatory protein active at only some of the promoters that are modulated by wild type NifA.

To determine if the amino acid changes identified in NifA were sufficient to cause the hydrogen production phenotype, two of the mutated nifA genes, one encoding the Q209P change and the other the M2021(change, were introduced by homologous recombination into the chromosome of a *R. palustris* strain that has a nifA deletion mutation. Both recombinant strains behaved similarly to the original nifA mutants and grew with cyclohexanecarboxylate as a carbon source, had nitrogenase activity, and produced hydrogen in the presence of ammonium (Table 4).

TABLE 4

Doubling time, nitrogenase activity and hydrogen production of recombinant nifA* mutants[a]

| Strain | Doubling time (cyclohexane-carboxylate)[b] | Nitrogenase activity[c] | Hydrogen production |
|---|---|---|---|
| CGA581 | 18 ± 3 | 74 ± 13 | 95 ± 36 |
| CGA584 | 17 ± 1 | 75 ± 23 | 101 ± 6 |

[a]Data are averages of at least three independent measurements, plus or minus standard deviation.
[b]Doubling times in hours.
[c]Nitrogenase activity in nmol $C_2H_4$ formed/min/mg protein. Cells were grown with 20 mM acetate in the presence of ammonium.
[d]Hydrogen production in μmol $H_2$/mg protein. Cells were grown with 5.7 mM cyclohexanecarboxylate in the presence of ammonium.

Transcriptome analysis of one of the recombinant strains revealed that it had elevated levels of gene expression that were similar in magnitude to those of the original hydrogen-producing mutant (Table 5).

TABLE 5

Selected genes expressed at higher levels in the recombinant nifA* strain CGA584 compared to wild type[a].

| RPA number | Fold change | Description |
|---|---|---|
| RPA0274 | 4.5 | GlnK, nitrogen regulatory protein P-II |
| RPA0275 | 4.5 | putative ammonium transporter AmtB |
| RPA1376 | 3.5 | nitrogenase iron protein, vnfH |
| RPA1927 | 29.2 | hypothetical protein |
| RPA1928 | 38.2 | ferredoxin-like protein [2Fe—2S] |
| RPA2156 | 33.3 | hypothetical protein |
| RPA2313 | 3.1 | Unknown protein |
| RPA2346 | 6.5 | hypothetical protein |
| RPA2347 | 3.7 | possible vanadium nitrogenase associated protein N (U51863) |
| RPA2348 | 3.0 | possible nitrogenase molybdenum-iron protein alpha chain (nitrogenase component I) (dinitrogenase) |
| RPA2353 | 3.1 | putative nitrogenase NifH subunit |
| RPA2354 | 4.0 | putative nitrogenase iron-molybdenum cofactor biosynthesis protein NifB |
| RPA3012 | 5.1 | light harvesting protein B-800-850, alpha chain D (antenna pigment protein, alpha chain D) (LH II-D alpha) |
| RPA3013 | 3.8 | light harvesting protein B-800-850, beta chain D (antenna pigment protein, beta chain D) (LH II-D beta) |
| RPA4602 | 29.1 | ferredoxin like protein, fixX |
| RPA4603 | 50.1 | Nitrogen fixation protein, fixC |
| RPA4604 | 108.4 | electron transfer flavoprotein alpha chain protein fixB |
| RPA4605 | 64.4 | electron transfer flavoprotein beta chain fixA |
| RPA4606 | 12.4 | nitrogenase stabilizer NifW |
| RPA4607 | 31.2 | putative homocitrate synthase |
| RPA4608 | 180.1 | nitrogenase cofactor synthesis protein nifS |
| RPA4609 | 40.6 | putative nifU protein |
| RPA4610 | 164.5 | Protein of unknown function, HesB YadR YfhF |
| RPA4611 | 16.3 | putative nitrogen fixation protein nifQ |
| RPA4612 | 15.1 | ferredoxin 2[4Fe—4S] III, fdxB |
| RPA4613 | 15.3 | DUF683 |
| RPA4614 | 20.5 | DUF269 |
| RPA4615 | 45.0 | nitrogenase molybdenum-iron protein nifX |
| RPA4616 | 21.8 | nitrogenase reductase-associated ferredoxin, nifN |
| RPA4617 | 25.5 | nitrogenase molybdenum-cofactor synthesis protein nifE |
| RPA4618 | 50.7 | nitrogenase molybdenum-iron protein beta chain, nifK |
| RPA4619 | 46.8 | nitrogenase molybdenum-iron protein alpha chain, nifD |
| RPA4620 | 85.9 | nitrogenase iron protein, nifH |
| RPA4621 | 12.5 | conserved hypothetical protein |
| RPA4622 | 42.5 | hypothetical protein |
| RPA4623 | 26.8 | conserved hypothetical protein |
| RPA4624 | 23.1 | hypothetical protein |
| RPA4625 | 132.4 | NifZ domain |
| RPA4626 | 9.4 | Protein of unknown function from Deinococcus and Synechococcus |
| RPA4627 | 13.7 | conserved hypothetical protein |
| RPA4628 | 27.0 | Protein of unknown function, HesB YadR YfhF |
| RPA4629 | 15.9 | ferredoxin 2[4Fe—4S], fdxN |
| RPA4630 | 15.1 | nitrogen fixation protein nifB |
| RPA4631 | 48.5 | ferredoxin 2[4Fe—4S], fdxN |
| RPA4633 | 16.2 | short-chain dehydrogenase |
| RPA4634 | 26.1 | hypothetical protein |
| RPA4714 | 16.5 | hypothetical protein |
| RPA4827 | 8.6 | conserved hypothetical protein |

[a]Cells were grown anaerobically in light with acetate under non-nitrogen-fixing conditions. Fold differences are relative to wild type grown anaerobically in light with acetate and ammonium sulfate (non-nitrogen-fixing conditions).

This indicates that the mutations identified in nifA are sufficient to activate all genes necessary for hydrogen production. It cannot be excluded that the strains may have additional mutations that contribute to the differences observed in growth, nitrogenase activity, and hydrogen production among the isolated mutant strains.

In addition to its molybdenum nitrogenase, R. palustris encodes vanadium and iron nitrogenases (Larimer, et al., "Complete Genome Sequence of the Metabolically Versatile Photosynthetic Bacterium Rhodopseudomonas palustris," Nat. Biotechnol. 22:55-61 (2004), which is hereby incorporated by reference in its entirety). Alternative nitrogenase synthesis depends on many of the cofactor synthesis and assembly proteins encoded by the nif gene cluster (Oda, et al., "functional Genomic Analysis of Three Nitrogenase Isozymes in the Photosynthetic Bacterium Rhodopseudomonas palustris," J. Bacteriol. 187:7784-94 (2005), which is hereby incorporated by reference in its entirety). Thus, it would be expected that a second mutation in addition to a nifA mutation would be necessary for constitutive synthesis of anf and vnf genes for alternative nitrogenases.

Development of a process for hydrogen production will likely depend on using whole bacterial cells as biocatalysts to efficiently supply ATP and electrons needed for nitrogenase activity. Hydrogen formation in the context of nitrogen fixation is wasteful for cells, because it represents a loss of reductant that could have been used for ammonia formation. In addition, anoxygenic photosynthetic bacteria accumulate nitrogenase mutations under conditions where the fixation of nitrogen gas into ammonia is not obligatory (Wall, et al., "Spontaneous Nif-Mutants of Rhodopseudomonas capsulate," J. Bacterial. 159:652-7 (1984), which is hereby incorporated by reference in its entirety). Here, a strategy is described to select for mutants of R. palustris for which hydrogen production is advantageous and required in order for cells to use electron-rich carbon sources for growth. This could be a useful trait in the context of an eventual commercial process as it provides a selection strategy that can be applied to maintain continuous hydrogen production.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of producing hydrogen, said method comprising:
   providing a microbe expressing a NifA protein comprising an activating mutation;
   wherein the activating mutation relieves GAF domain repression of NifA transactivating activity and results in constitutive transactivation of a gene in a nitrogenase gene cluster;
   wherein the activating mutation comprises a mutation located in the linker region between the GAF regulatory domain and the AAA$^+$ ATPase domain;
   and incubating the microbe in a culture medium under conditions effective for the microbe to produce hydrogen;
   thereby providing increased hydrogen production.

2. The method of claim 1, wherein the microbe strain is an anoxygenic photosynthetic bacterium.

3. The method of claim 2, wherein the microbe strain is a microbe of the genus selected from the group consisting of *Rhodopseudomonas, Blastochloris, Rhodobacter, Rhodospirillium, Rubrivirax, Rhodomicrobium, Rhodoferax* and *Rhodocyclus*.

4. The method of claim 3, wherein the microbe strain is *Rhodopseudomonas palustris*.

5. The method of claim 1, wherein expression of said NifA protein permits increased hydrogenase activity by said microbe.

6. The method of claim 1, wherein expression of said NifA protein permits increased nitrogenase activity by said microbe.

7. The method of claim 1, wherein the activating mutation renders the protein competent to increase nitrogenase gene expression.

8. The method of claim 1, wherein the microbe is a recombinant strain.

9. The method of claim 1, wherein said incubating is carried out under anaerobic conditions, in the presence of light, in an electron-rich carbon containing culture medium under non-nitrogen fixing conditions.

10. The method of claim 9, wherein the electron-rich carbon is a reduced carbon.

11. The method of claim 10, wherein the reduced carbon is selected from the group consisting cyclohexanecarboxylate, acetate, p-coumarate, succinate, ethanol, toluene, benzoate, butyrate, and butanol.

12. The method of claim 1, wherein said culture medium contains a form of nitrogen that represses nitrogenase activity.

13. The method of claim 12, wherein the form of nitrogen that represses nitrogenase activity is ammonium sulfate.

14. The method of claim 1 wherein the activating mutation comprises a mutation that changes at least one amino acid residue in said NifA protein relative to SEQ ID NO: 1.

15. The method of claim 1, wherein the mutation in NifA located in the linker region between the GAF regulatory domain and the AAA$^+$ ATPase domain changes the polarity of the affected position.

16. The method of claim 1, wherein the microbe comprises a nucleic acid molecule encoding NifA with an activating mutation relative to the NifA-encoding nucleic acid sequence of SEQ ID NO: 2.

17. The method of claim 16, wherein the activating mutation results in one or more amino acid substitutions in SEQ ID NO: 1 selected from the group consisting of $Q^{209} \rightarrow P$, $M^{202} \rightarrow K$, $L^{212} \rightarrow R$, $S^{213} \rightarrow P$, and combinations thereof.

* * * * *

SEQUENCE LISTING

<160> NUMBER OF SEQ ID NOS: 2

<210> SEQ ID NO 1
<211> LENGTH: 584
<212> TYPE: PRT
<213> ORGANISM: Rhodopseudomonas palustris

<400> SEQUENCE: 1

```
Met Ala Gln Arg Glu Ile Arg Leu Val Asp Asn Glu Tyr Pro Ser Pro
1               5                   10                  15

Ser Met Thr His Pro Pro Ile Pro Leu Ser Asp Ile Ala Leu Thr Gly
            20                  25                  30

Ile Phe Glu Ile Ser Lys Ile Leu Thr Ser Pro Ala Arg Leu Glu Ile
        35                  40                  45

Thr Leu Ala Asn Val Val Asn Leu Leu Gln Ser Phe Leu Gln Met Arg
    50                  55                  60

Asn Gly Val Val Ser Leu Leu Ala Asp Asp Gly Val Pro Asp Ile Thr
65                  70                  75                  80

Val Gly Val Gly Trp Asn Glu Gly Ser Asp Asn Arg Tyr Arg Ala Arg
                85                  90                  95

Leu Pro Gln Lys Ala Ile Asp Gln Ile Val Ala Thr Ala Val Pro Leu
            100                 105                 110

Val Ala Asp Asn Val Ser Ala His Pro Met Phe Thr Ala Ala Asp Ala
        115                 120                 125

Met Ala Leu Gly Ala Thr Asp Glu Ile Arg Val Ser Phe Ile Gly Val
    130                 135                 140

Pro Ile Arg Ile Asp Ser Arg Val Val Gly Thr Leu Ser Ile Asp Arg
145                 150                 155                 160

Val Arg Asp Gly Arg Ser His Phe Arg Met Asp Ala Asp Val Arg Phe
                165                 170                 175

Leu Thr Met Val Ala Asn Leu Ile Gly Gln Thr Val Lys Leu His Arg
            180                 185                 190

Val Val Ala Arg Asp Arg Glu Arg Leu Met Ala Glu Ser His Arg Leu
        195                 200                 205

Gln Lys Glu Leu Ser Glu Leu Lys Pro Glu Arg Glu Arg Lys Arg Val
    210                 215                 220

Lys Val Asp Gly Ile Val Gly Glu Ser Pro Ala Ile Arg Lys Leu Leu
225                 230                 235                 240

Ala Lys Val Ser Ile Ile Ala Lys Ser Gln Ser Pro Val Leu Leu Arg
                245                 250                 255

Gly Glu Ser Gly Thr Gly Lys Glu Leu Ile Ala Lys Ala Ile His Glu
            260                 265                 270

Leu Ser Ala Arg Ala Asn Gly Pro Phe Ile Lys Ile Asn Cys Ala Ala
        275                 280                 285

Leu Pro Glu Ser Val Leu Glu Ser Glu Leu Phe Gly His Glu Lys Gly
    290                 295                 300

Ala Phe Thr Gly Ala Ile Ala Ser Arg Lys Gly Arg Phe Glu Leu Ala
305                 310                 315                 320

Asp Lys Gly Thr Leu Phe Leu Asp Glu Ile Gly Glu Ile Ser Ala Ser
                325                 330                 335

Phe Gln Ala Lys Leu Leu Arg Val Leu Gln Glu Gln Glu Phe Glu Arg
            340                 345                 350

Val Gly Gly Asn Gln Thr Ile Lys Val Asn Val Arg Ile Val Ala Ala
        355                 360                 365
```

```
Thr Asn Arg Asn Leu Glu Glu Ala Val Ala Arg Lys Glu Phe Arg Ala
    370                 375                 380

Asp Leu Tyr Tyr Arg Ile Asn Val Val Pro Met Ile Leu Pro Pro Leu
385                 390                 395                 400

Arg Asp Arg Pro Ser Asp Ile Pro Leu Leu Ala Ser Glu Phe Leu Lys
                405                 410                 415

Asn Phe Asn Lys Glu Asn Gly Arg Glu Leu Ala Phe Gly Ser His Ala
                420                 425                 430

Leu Asp Leu Leu Lys Ala Cys Ser Phe Pro Gly Asn Val Arg Glu Leu
                435                 440                 445

Glu Asn Cys Val Arg Arg Thr Ala Thr Leu Ala Met Gly Pro Glu Ile
    450                 455                 460

Arg Asp Ser Asp Phe Ala Cys His Gln Asp Glu Cys Leu Ser Ala Ile
465                 470                 475                 480

Leu Trp Lys Gly His Ala Glu Pro Ala Pro Glu Arg Pro Arg Pro Glu
                485                 490                 495

Ile Pro Leu Gln Val Leu Pro Arg Lys Ala Pro Val Glu Ile Val His
                500                 505                 510

Pro Arg Glu Pro Val Ala Ser Ala Asp Asp Phe Ala Pro Ala Pro Val
                515                 520                 525

Arg Ser Glu Met Pro Ser Asp Glu Ser Asn Met Ser Glu Arg Glu Arg
    530                 535                 540

Leu Ile Asn Ala Met Glu Arg Ala Gly Trp Val Gln Ala Lys Ala Ala
545                 550                 555                 560

Arg Ile Leu Gly Leu Thr Pro Arg Gln Ile Gly Tyr Ala Leu Lys Lys
                565                 570                 575

His Asn Ile Glu Leu Lys His Phe
                580

<210> SEQ ID NO 2
<211> LENGTH: 1755
<212> TYPE: DNA
<213> ORGANISM: Rhodopseudomonas palustris

<400> SEQUENCE: 2
atggctcagc gcgaaattcg ccttgtcgat aacgagtacc cgtcgccttc gatgacccat    60
cctccgatac cgctgagtga catcgcgctc accggcattt tcgagatctc gaaaatcctc   120
acctcaccgg cgcggttgga gatcacccct gccaacgtcg tcaacctgct gcagtcattt   180
ttgcagatgc gcaacggcgt ggtgtcgctg ctcgccgatg acggcgtgcc cgatattacc   240
gtcggggtcg gctggaatga ggggagcgat aaccgctatc gcgcccggct gccgcagaag   300
gcgatcgacc agatcgtcgc gaccgcggtg ccgctggtcg ccgacaacgt ctccgcccac   360
ccgatgttca ccgcggccga cgctatggcg ctcggcgcaa ctgacgaaat ccgggtgtcg   420
ttcatcggcg tgccgatccg gatcgactcg cgggtggtgg ggacgctgag catcgaccgc   480
gtccgcgatg gccgttcgca cttccggatg gacgccgacg tgcgcttcct caccatggtg   540
gccaatctga tcgccaaac cgtgaagctg caccgcgtcg tcgcccgcga ccgcgagcgg   600
ctgatggcgg aaagccaccg gctgcagaag gaactgtccg agctgaagcc ggagcgcgag   660
cgtaagcggg tcaaggtcga cggcatcgtc ggcgagagcc cggcgatccg caaattgctg   720
gccaaggtca gcatcatcgc caagtcgcag tcgcccgtgt tgctgcgcgg cgagtcggga   780
accggcaagg agctgatcgc aaaagcgatc acgaattgt cggcgcgcgc caacggcccg   840
ttcatcaaga tcaactgcgc ggcgctgccg gaatcggtgc tggagtccga gctgttcggg   900
```

```
cacgagaagg gcgccttcac cggcgcgatc gcctcgcgca agggccggtt cgagctggcc      960
gacaagggca cgctgtttct cgacgagatc ggtgagatct ccgcgtcgtt ccaggccaag     1020
ctgctgcgcg tcttgcagga gcaggaattc gaacgggtcg gcggcaacca gaccatcaag     1080
gtcaatgtcc ggatcgtcgc cgccaccaac cgcaatctgg aagaggcagt ggcgcgcaag     1140
gaattccgcg ccgatctgta ttaccgcatc aatgtagtgc cgatgatcct gccgccgctg     1200
cgcgaccggc ccagcgacat cccgctgctg gcgagcgaat tcctgaagaa cttcaacaag     1260
gagaacggcc gcgagctggc cttcgagtcg cacgcgctgg atctgctgaa ggcctgctcg     1320
ttccccggca acgtccgcga gctggagaac tgcgtgcgcc gcaccgcgac cctggcgatg     1380
gggccggaaa tccgcgacag cgatttcgcc tgtcaccagg acgaatgcct gtcggcgatc     1440
ctgtggaagg gtcacgccga acctgcgccc gagcgcccac gccctgagat cccgttgcag     1500
gtcctgccgc gcaaggcgcc ggtggaaatc gtccatccgc gcgagccggt cgcatcagcg     1560
gatgattttg cgccggcgcc ggttcgttcc gagatgccat ccgacgaatc gaacatgtcg     1620
gagcgcgagc ggctgatcaa cgccatggag cgagccgggt gggtgcaggc gaaggccgca     1680
cgcattctcg gcctcacgcc gcgccagatc ggctacgcgc tgaagaagca caacatcgag     1740
ctcaagcact tctga                                                      1755
```